US010738280B2

United States Patent
Okano et al.

(10) Patent No.: US 10,738,280 B2
(45) Date of Patent: Aug. 11, 2020

(54) METHOD FOR PRODUCING NAÏVE PLURIPOTENT STEM CELLS

(71) Applicants: ONO PHARMACEUTICAL CO., LTD., Osaka (JP); KEIO UNIVERSITY, Tokyo (JP)

(72) Inventors: Hideyuki Okano, Tokyo (JP); Seiji Shiozawa, Tokyo (JP); Fumihiko Kisa, Ibaraki (JP)

(73) Assignees: ONO PHARMACEUTICAL CO., LTD., Osaka (JP); KEIO UNIVERSITY, Tokyo (JP)

( * ) Notice: Subject to any disclaimer, the term of this patent is extended or adjusted under 35 U.S.C. 154(b) by 187 days.

(21) Appl. No.: 15/558,473

(22) PCT Filed: Mar. 17, 2016

(86) PCT No.: PCT/JP2016/058577
§ 371 (c)(1),
(2) Date: Sep. 14, 2017

(87) PCT Pub. No.: WO2016/148253
PCT Pub. Date: Sep. 22, 2016

(65) Prior Publication Data
US 2018/0080009 A1 Mar. 22, 2018

(30) Foreign Application Priority Data
Mar. 18, 2015 (JP) .................................. 2015-054907

(51) Int. Cl.
| C12N 5/00 | (2006.01) |
| C12N 5/02 | (2006.01) |
| C12N 5/074 | (2010.01) |
| C12N 5/10 | (2006.01) |
| C12N 15/09 | (2006.01) |

(52) U.S. Cl.
CPC ............. *C12N 5/0696* (2013.01); *C12N 5/10* (2013.01); *C12N 15/09* (2013.01); *C12N 2501/01* (2013.01); *C12N 2501/20* (2013.01); *C12N 2501/60* (2013.01); *C12N 2501/602* (2013.01); *C12N 2501/603* (2013.01); *C12N 2501/605* (2013.01); *C12N 2501/606* (2013.01)

(58) Field of Classification Search
CPC .................................................. C12N 5/0696
See application file for complete search history.

(56) References Cited

U.S. PATENT DOCUMENTS

| 2009/0068742 A1 | 3/2009 | Yamanaka |
| 2015/0037883 A1 | 2/2015 | Baharvand et al. |

FOREIGN PATENT DOCUMENTS

| JP | 2014-217344 A | 11/2014 |
| WO | 2011/047300 A1 | 4/2011 |
| WO | 2012/087965 A2 | 6/2012 |
| WO | 2012/087965 A3 | 6/2012 |
| WO | 2014/181682 A1 | 11/2014 |

OTHER PUBLICATIONS

Nichols, 2009, Cell Stem Cell, 4:487-492.*
Gafni (2013, Nature, 504:282-286).*
Welling (2013, Trends in Cell Biology, 23:442-448).*
Van Der Jeught, et al., "The Combination of Inhibitors of FGF/MEK/Erk and GSK3β Signaling Increases the Number of OCT3/4- and NANOG-Positive Cells in the Human Inner Cell Mass, But Does Not Improve Stem Cell Derivation" 2013, Stem Cells and Development, vol. 22, Issue No. 2, 11 pages total, XP 055247715.
Hirano, et al., "Human and Mouse Induced Pluripotent Stem Cells Are Differentially Reprogrammed in Response to Kinase Inhibitors", 2012, Stem Cells and Development, vol. 21, Issue No. 8, 14 pages total, XP 055242620.
Communication dated Jul. 6, 2018, issued by the European Patent Office in counterpart European Patent Application No. 16765082.9.
Yasuhiro Takashima, et al., "Resetting Transcription Factor Control Circuitry toward Ground-State Pluripotency in Human", Cell, Sep. 11, 2014, vol. 158, pp. 1254-1269.
Fumihiko Kisa, et al., "Hito iPS Saibo ni Okeru Tanosei Jotai no Kaihen (P-01-006: Changes in pluripotent state in human iPS cells)", Regenerative Medicine, Feb. 2015, vol. 14, Suppl., total 3 pages.
Seiji Shiozawa, et al. "Common Marmoset Es Saibo ni Okeru Tanosei Jotai no Kaihen (P-01-004: Changes in pluripotent state in common marmoset ES cells )", Regenerative Medicine, Feb. 2015, vol. 14, Suppl., total 3 pages.
Jacob Hanna, et al., "Human embryonic stem cells with biological and epigenetic characteristics similar to those of mouse ESCs", PNAS, May 18, 2010, vol. 107, No. 20, p. 9222-9227.
Seyedeh-Nafiseh Hassani, et al., "Inhibition of TGFβ Signaling Promotes Ground State Pluripotency", Stem Cell Rev and Rep, vol. 10, 2014 pp. 16-30.
Christa Buecker et al., "A Murine ESC-like State Facilitates Transgenesis and Homologous Recombination in Human Pluripotent Stem Cells", Cell Stem Cell, Jun. 4, 2010, vol. 6, pp. 535-546.

(Continued)

*Primary Examiner* — Valarie E Bertoglio
(74) *Attorney, Agent, or Firm* — Sughrue Mion, PLLC

(57) ABSTRACT

To produce and/or maintain naïve pluripotent stem cells capable of highly expressing genes important for maintaining an undifferentiated state, which could not be achieved by known methods for producing pluripotent stem cells. The present invention can produce naïve pluripotent stem cells capable of maintaining an undifferentiated state by introducing and allowing transient expression of six genes (Oct3/4, Klf4, c-Myc, Sox2, Nanog, and Klf2) among the so-called initializing factors, and further performing culturing in a medium containing LIF, an MEK inhibitor, a GSK3 inhibitor, a cAMP production promoter, a TGF-β inhibitor and a PKC inhibitor. Thus, the problem of the present invention can be solved.

10 Claims, 9 Drawing Sheets

Specification includes a Sequence Listing.

(56) References Cited

OTHER PUBLICATIONS

Peipei Song, et al., "Perspectives on human clinical trials of therapies using iPS cells in Japan: Reaching the forefront of stem-cell therapies", BioScience Trends. 2013; vol. 7, No. 3, pp. 157-158.
Jennifer Nichols, et al., "Naive and Primed Pluripotent States", Cell Stem Cell, Perspective, vol. 4, Jun. 5, 2009, pp. 487-492.
Bo Feng, et al., "Reprogramming of fibroblasts into induced pluripotent stem cells with orphan nuclear receptor Esrrb", Nature Cell Biology, vol. 11, No. 2, Feb. 2009, total 20 pages.
International Search Report (PCT/ISA/210) dated Jun. 21, 2016 issued by the International Searching Authority in counterpart International Application No. PCT/JP2016/058577.
Written Opinion in English (PCT/ISA/237) dated Jun. 21, 2016 issued by the International Searching Authority in counterpart International Application No. PCT/JP2016/058577.

\* cited by examiner

METHOD FOR PRODUCING NAÏVE PLURIPOTENT STEM CELLS

TECHNICAL FIELD

The present invention relates to a method for producing and/or maintaining a naïve-state pluripotent stem cells (hereinafter, also abbreviated as a "method of the present invention"). The present invention also relates to naïve pluripotent stem cells produced and/or maintained by the method of the present invention and having excellent pluripotency.

BACKGROUND ART

In recent years, in the field of regeneration medicine, with the advent of technology of induced pluripotent stem cells (hereinafter, also abbreviated as "iPS cells"), clinical studies toward practical use of iPS cells are rapidly progressing. For example, clinical tests to age-related macular degeneration patients are already carried out using retinal pigment epithelium cells induced from human iPS cells. In addition, clinical tests using nerve cells, chondrocytes, and the like, derived from human iPS cells are planned to be carried out (see, Non-Patent Literature 1).

The iPS cells are one type of pluripotent stem cells. The pluripotent stem cells include embryonic stem cells (hereinafter, also abbreviated as ES cells), and Epiblast Stem cells, in addition to the iPS cells. In recent years, these pluripotent stem cells have been known to have different basic characteristics depending on differences in animal species from which cells are derived or types of pluripotent stem cells. Specifically, mouse ES cells and mouse iPS cells are close to the early stage of development, can be easily cultured or genetically engineered, and highly proliferate, thus enabling differentiation to be induced efficiently. Such cells are called naïve cells. On the other hand, human ES cells, human iPS cells, and the like, represent epiblast characteristics in a highly-developed stage. Therefore, it is difficult to genetically engineer the cells, and differentiation is biased toward any one specific germ-layer among three germ-layers. Such cells are called primed cells (see, Non-Patent Literature 2). Therefore, in regeneration medicine etc., in order to practically use pluripotent stem cells, a producing method capable of reliably obtaining pluripotent stem cells having characteristics of the naïve state rather than characteristics of the primed state has been demanded.

As a method for producing human iPS cells, a method of introducing so-called Yamanaka four factors (Oct3/4 gene, Sox2 gene, Klf4 gene, and c-Myc gene) into somatic cells (see, Patent Literature 1) has been known. However, the method had a problem that only primed human iPS cells were able to be produced. To date, in order to produce naïve human iPS cells, techniques to induce iPS cells derived from various animals to a naïve state have been developed. Attempt to further introduce other genes into the above-mentioned Yamanaka four factors, and consideration of medium conditions by adding various compounds, have been carried out. For example, in a method of introducing two factors, Nanog and Klf2, and adding LIF (Leukemia inhibitory factor), PD0325901 (MEK inhibitor), CHIR99021 (GSK3 inhibitor) and Go6983 (PKC inhibitor) into a medium (see Non-Patent Literature 3), expression of KLF4 and TFCP2L1 which are known to be naïve gene markers is increased, and, therefore, obtaining of human iPS cells in a state close to the naïve state is reported.

However, the above-mentioned technology has a problem that expression of ESRRB (Estrogen-related receptor beta) that is considered to be a gene important for maintaining of a naïve undifferentiated state is hardly observed (see Non-Patent Literatures 3 and 4), and the like.

PRIOR ART LITERATURES

Patent Literatures

Patent Literature 1: Japanese Patent Publication No. 4183742

Non-Patent Literatures

Non-Patent Literature 1: BioScience Trends, Vol. 7, No. 3, pages 157-158, 2013
Non-Patent Literature 2: Cell Stem Cell, Vol. 4, pages 487-492, 2009
Non-Patent Literature 3: Cell, Vol. 158, page 1254-1269, 2014
Non-Patent Literature 4: Nature Cell Biology, Vol. 11, No. 2, page 197-203, 2009

SUMMARY OF INVENTION

Technical Problem

The problem of the present invention is to produce and/or maintain pluripotent stem cells capable of high expression of genes important for maintaining of a naïve undifferentiated potential.

Solution to Problem

In order to solve the above-mentioned problem, the inventors of the present invention have extensively studied. As a result, surprisingly, the inventors have found a method for producing pluripotent stem cells capable of maintaining a naïve undifferentiated state by introducing six genes (Oct3/4, Klf4, c-Myc, Sox2, Nanog, and Klf2) among the so-called initializing factors to allow the genes to transiently express, and further performing culturing in a medium containing LIF, an MEK inhibitor, a GSK3 inhibitor, a cAMP production promoter, a TGF-β inhibitor, and a PKC inhibitor, and have completed the present invention.

The present invention relates to: [1] a method for producing naïve pluripotent stem cells, the method including: allowing transient expression of two types of genes: Nanog and Klf2 in primed pluripotent stem cells, and performing culturing in a medium containing LIF, an MEK inhibitor, a GSK3 inhibitor, a cAMP production promoter, a TGF-β inhibitor, and a PKC inhibitor,

[2] the producing method described in the above [1], wherein the primed pluripotent stem cells are primed induced pluripotent stem cells or primed embryonic stem cells,

[3] the method for producing naïve human pluripotent stem cells described in the above [1] or [2], wherein the primed pluripotent stem cells are primed human induced pluripotent stem cells or primed human embryonic stem cells,

[4] the method for producing naïve human induced pluripotent stem cells described in any one of the above [1] to [3], wherein the primed pluripotent stem cells are the primed human induced pluripotent stem cells,

[5] the producing method described in any one of the above [1] to [4], further including a step of allowing transient expression of the following four genes: Oct3/4, Klf4, c-Myc, and Sox2,

[6] the producing method described in any one of the above [1] to [5], wherein the MEK inhibitor is PD0325901, the GSK3 inhibitor is CHIR99021, the cAMP production promoter is Forskolin, the TGF-β inhibitor is A83-01, and the PKC inhibitor is Go6983,

[7] the producing method described in any one of the above [1] to [6], wherein the medium is an N2B27 medium,

[8] a method for producing naïve pluripotent stem cells, the method including a step of allowing transient expression of the following six genes: Nanog, Klf2, Oct3/4, Klf4, c-Myc, and Sox2 in primed pluripotent stem cells,

[9] the producing method described in the above [8], wherein the primed pluripotent stem cells are primed induced pluripotent stem cells or primed embryonic stem cells,

[10] the method for producing naïve human pluripotent stem cells described in the above [8] or [9], wherein the primed pluripotent stem cells are primed human induced pluripotent stem cells or primed human embryonic stem cells,

[11] the method for producing naïve human induced pluripotent stem cells described in any one of the above [8] to [10], wherein the primed pluripotent stem cells are primed human induced pluripotent stem cells,

[12] a method for producing naïve induced pluripotent stem cells, the method comprising a step of allowing transient expression of the following six genes: Nanog, Klf2, Oct3/4, Klf4, c-Myc, and Sox2 in somatic cells,

[13] the producing method described in the above [12], further including allowing transient expression of six genes: Oct3/4, Klf4, c-Myc, Sox2, Nanog, and Klf2 in somatic cells and performing culturing in a medium containing LIF, an MEK inhibitor, a GSK3 inhibitor, a cAMP production promoter, a TGF-β inhibitor and a PKC inhibitor,

[14] the method for producing naïve human induced pluripotent stem cells described in the above [12] or [13], wherein the somatic cells are human-derived somatic cells,

[15] the producing method described in the above [13] or [14], wherein the MEK inhibitor is PD0325901, the GSK3 inhibitor is CHIR99021, the cAMP production promoter is Forskolin, the TGF-β inhibitor is A83-01, and the PKC inhibitor is Go6983,

[16] the producing method described in any one of the above [13] to [15], wherein the medium is an N2B27 medium,

[17] a method for maintaining naïve pluripotent stem cells, the method comprising culturing the naïve pluripotent stem cells in a medium containing LIF, an MEK inhibitor, a GSK3 inhibitor, a cAMP production promoter, a TGF-β inhibitor and a PKC inhibitor,

[18] the maintaining method described in the above [17], wherein the naïve pluripotent stem cells are naïve induced pluripotent stem cells or naïve embryonic stem cells,

[19] the method for maintaining naïve human pluripotent stem cells described in the above [17] or [18], wherein the naïve pluripotent stem cells are naïve human induced pluripotent stem cells or naïve human embryonic stem cells,

[20] the method for maintaining naïve human induced pluripotent stem cells described any one of in the above [17] to [19], wherein the naïve pluripotent stem cells are naïve human induced pluripotent stem cells,

[21] The maintaining method described in any one of the above [17] to [20], wherein the MEK inhibitor is PD0325901, the GSK3 inhibitor is CHIR99021, the cAMP production promoter is Forskolin, the TGF-β inhibitor is A83-01, and the PKC inhibitor is Go6983,

[22] the maintaining method described in any one of the above [17] to [21], wherein the medium is an N2B27 medium.

[23] a naïve pluripotent stem cell produced by the method described in any one of the above [1] to [16],

[24] a naïve pluripotent stem cell maintained by the method described in any one of the above [17] to [22], and the like.

Advantageous Effects of Invention

According to a method for producing pluripotent stem cells cultured in specific conditions of the present invention, it is possible to stably produce pluripotent stem cells maintaining characteristics of the naïve state and having pluripotency.

DESCRIPTION OF EMBODIMENTS

Figure 1:
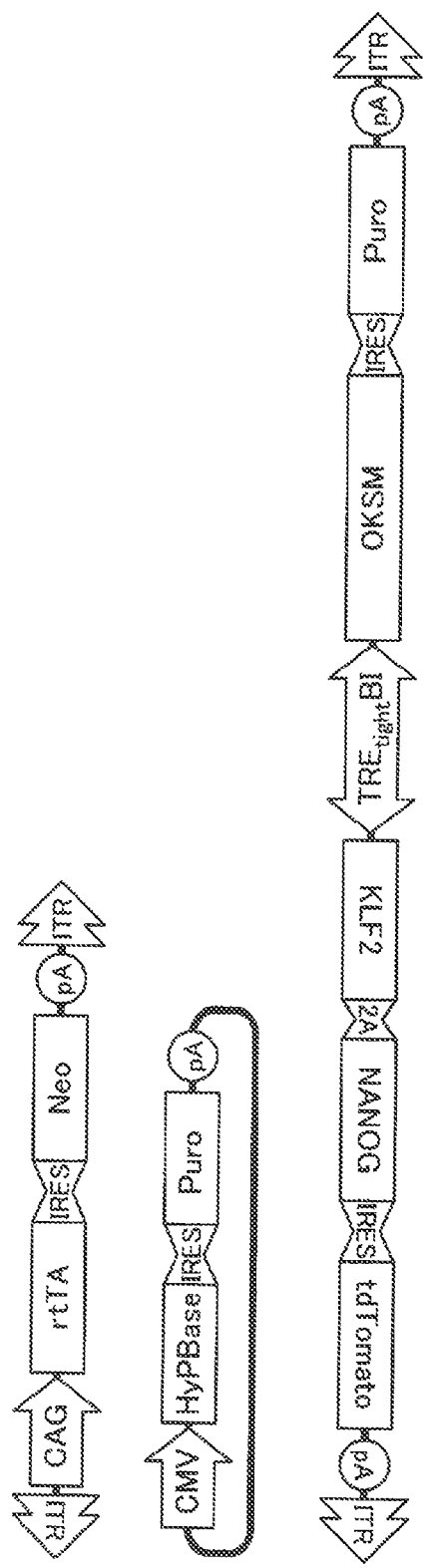
FIG. 1 shows a gene expression vector used for gene introduction.

The present invention will be described in detail hereinafter.

In the present invention, a method for producing naïve pluripotent stem cells is carried out according to the following steps. In other words, the naïve pluripotent stem cells are produced through the steps including: step (i): a step of introducing a certain gene into somatic cells or primed pluripotent stem cells using a gene expression vector; step (ii): a step of culturing the somatic cells or the primed pluripotent stem cells into which the gene has been introduced in the step (i) in a prime medium, adding doxycycline thereto, and then cloning a gene expression cell line; step (iii): a step of allowing transient expression of the gene introduced in the step (i) in the gene expression cell line cloned in the step (ii), and, during the time, performing culturing in a naïve medium into which various compounds were added.

Furthermore, in the present invention, a method for maintaining naïve pluripotent stem cells includes culturing and subculturing naïve pluripotent stem cells in a naïve medium containing various compounds.

In the present invention, the somatic cells are not particularly limited, and any somatic cells can be used. For example, in addition to somatic cells at an embryonic stage, mature somatic cells may be used. Examples of the somatic cells include differentiated cells including (1) tissue stem cells (somatic stem cells) such as neural stem cells, hematopoietic stem cells, mesenchymal stem cells, and dental pulp stem cells, (2) tissue precursor cells, (3) fibroblasts (skin cells, etc.), epithelial cells, liver cells, lymphocytes (T cells and B cells), endothelial cells, muscular cells, hair cells, gastric mucosa cells, intestine cells, splenic cells, pancreatic cells (pancreatic outer secretion cells, etc.), brain cells, pneumocytes, nephrocytes, skin cells, and the like. Preferable somatic cells are human-derived somatic cells.

In the present invention, the pluripotent stem cells are not particularly limited, and examples thereof include embryonic stem cells (ES cells), nuclear-transfer embryonic stem (ntES) cells derived from cloned embryo, germline stem cells (GS cell), epiblast cells, embryonic germ cells (EG cells), multipotent germline stem cells (mGS cells), and induced pluripotent stem cells (iPS cells). Among them, ES cells, ntES cells, and iPS cells are preferable, ES cells and iPS cells are more preferable, and iPS cells are particularly preferable.

Herein, living bodies from which these somatic cells or pluripotent stem cells are derived are not particularly limited, and examples thereof include human, non-human animals (for example, monkey, sheep, cow, horse, dog, cat, rabbit, rat, and mouse). A preferable example is human.

In the present invention, the primed pluripotent stem cells are not particularly limited, but they mean cells excluding mouse ES cells and mouse iPS cells which are recognized to be naïve cells among the pluripotent stem cells. Example include ES cells and iPS cells derived from human, monkey, pig, sheep, dog, and cow, as well as epiblast stem cells derived from human and non-human animal cells mentioned above. Preferable examples include human ES cells and human iPS cells, and particularly preferable example is human iPS cells.

In the present invention, the cell line of human ES cells to be used as the primed pluripotent stem cells is not particularly limited, and examples thereof include H1, H9, Shef6, khES-1, khES-2, khES-3, khES-4, and khES-5.

In the present invention, the cell line of the human iPS cells used as the primed pluripotent stem cells is not particularly limited, and examples thereof include WD39 (derived from fibroblast), aTKA4 (derived from T cells), 201B6, 201B7, 253G1, and 253G4. Among them, WD39 or 201B7 is preferable.

In the present invention, genes to be introduced into somatic cells or primed pluripotent stem cells are not particularly limited as long as they are factors that are known as initializing factors (reprogramming factors). Examples thereof include Oct3/4, Klf4, c-Myc, Sox2, Nanog, Klf2, L-Myc, N-Myc, Klf5, Lin28, Tert, Fbx15, ERas, ECAT15-1, ECAT15-2, Tcl1, β-Catenin, ECAT1, Esg1, Dnmt3L, ECAT8, Gdf3, Sox15, Fth117, Sal14, Rex1, UTF1, Stella, Stat3, Grb2, Prdm14, Nr5a1, Nr5a2, and E-cadherin. Herein, optional combination of two or more genes selected from the gene group can be introduced. Among them, the combination of Oct3/4, Klf4, c-Myc, Sox2, Nanog, and Klf2 is preferable. However, when the cells into which genes are to be introduced are primed pluripotent stem cells, since any of the above-mentioned initializing factors are expressed, initializing factors excluding the expressed factors may be introduced. When the cells are human ES cells or human iPS cells as the initializing factors, for example, a combination of Nanog and Klf2 is preferable, and a combination of Oct3/4, Klf4, c-Myc, Sox2, Nanog, and Klf2 is furthermore preferable. Furthermore, species of introducing cells are preferably the same as the species of the cells into which genes are to be introduced. Examples of the genes to be introduced into human-derived cells preferably include human genes. Example of the genes to be introduced into human-derived somatic cells, human ES cells, or human iPS cells include preferably a combination of human Nanog (NANOG), and human Klf2 (KLF2), and further preferably a combination of human Oct3/4 (OCT3/4), human Klf4 (KLF4), human c-Myc (c-MYC), human Sox2 (SOX2), human Nanog (NANOG), and human Klf2 (KLF2).

In the present invention, the gene expression vectors are not particularly limited, and examples thereof include a virus vector, a plasmid vector, an artificial chromosome vector, and a transposon vector. Examples of the virus vector include a retrovirus vector, an adenovirus vector, a Sendai virus vector, a lentivirus vector, and an adeno-associated virus vector.

In the present invention, after somatic cells or primed pluripotent stem cells are subjected to gene introduction, they may be cultured together with feeder cells. The feeder cells are not particularly limited, and examples thereof include mouse embryonic fibroblast cells (MEF cells), mouse embryonic fibroblast line (STO cells), and the like.

In the present invention, the prime medium is not particularly limited, and examples thereof include a medium prepared by combining any of additive components such as replacement serum (KSR; Knockout™ Serum Replacement (Invitrogen)), fetal bovine serum (FBS), non-essential amino acid (NEAA), L-glutamine, 2-mercaptoethanol, antibiotics (for example, streptomycin, penicillin, puromycin, and mitomycin), and bFGF (basic Fibroblast Growth Factor), and adding any combination into a basal medium that is preferably DMEM (Dulbecco Modified Eagle medium), a mixer medium of DMEM and F12 (DMEM/F12=1:1), and Knockout™ D-MEM (available from Invitrogen).

In the present invention, cloning refers to a method of screening cells in which expression of genes is recognized in any of the somatic cells or primed pluripotent stem cells into which initializing factors have been gene-introduced. Examples of such screening method include a method of verifying fluorescence of a fluorescent protein gene which was incorporated into a gene expression vector in advance under fluorescence microscope. Examples of the fluorescence include a green fluorescent protein (GFP) gene, yellow fluorescent protein (YFP) gene (for example, Venus), a cyan fluorescent protein (CFP) gene (for example, Cerulean), a red fluorescent protein (RFP) gene (for example, TOMATO), and the like. Cells screened by this method is called a gene expression cell line in the present invention.

In the present invention, various compounds in the step (iii) and the maintaining method include a LIF (Leukemia inhibitory factor), an MEK inhibitor, a GSK3 inhibitor, a cAMP production promoter, a TGF-β inhibitor, or a PKC inhibitor. It is preferable that all of these compounds are added to a naïve medium.

In the present invention, the MEK inhibitor is not particularly limited, and examples thereof include PD0325901 (N-[(2R)-2,3-dihydroxypropoxy]-3,4-difluoro-2-[(2-fluoro-4-iodophenyl)amino]-benzamide; CAS registry number: 391210-10-9), U0126 (1,4-diamino-2,3-dicyano-1,4-bis[2-aminophenylthio]butadien e; CAS registry number: 109511-58-2), PD98059 (2-(2-amino-3-methoxyphenyl)-4H-1-benzopyran-4-one; CAS registry number: 167869-21-8), PD184352 (2-(2-chloro-4-iodo phenylamino)-N-cyclopropylmethoxy-3,4-difluorobenzamide; CAS registry number: 212631-79-3, and the like. Especially, PD0325901 is preferable.

In the present invention, the GSK3 inhibitor is not particularly limited, and examples thereof include CHIR99021 (6-[[2-[[4-(2,4-dichlorophenyl)-5-(5-methyl-1H-imidazole-2-yl)-2-pyrimidinyl]amino]ethyl]amino]-3-pyridinecarbonitrile; CAS registry number: 252917-06-9), BIO (6-bromoindirubin-3'-oxime; CAS registry number: 667463-62-9), Kenpaullone (9-bromo-7,12-dihydroindolo[3,2-d][1]benzazepin-6(5H)-one; CAS registry number: 142273-20-9), IM-16 (3-(4-fluorophenylethyl amino)-1-methyl-4-(2-methyl-1H-indole-3-yl)-1H-pyrrole-2,5-dione; CAS registry number: 1129669-05-1), and the like. Especially, CHIR99021 is preferable.

In the present invention, the cAMP production promoter is not particularly limited, and examples thereof include Forskolin (CAS registry number: 66428-89-5), and the like.

In the present invention, the TGF-β inhibitor is not particularly limited, and examples thereof include A83-01 (3-(6-methyl-2-pyridinyl)-N-phenyl-4-(4-quinolinyl)-1H-pyrazole-1-carbothioamide; CAS registry number: 909910-43-6), SB431542 (4-[4-(1,3-benzodioxole-5-yl)-5-(2-pyridinyl)-1H-imidazole-2-yl]-benzamide; CAS registry number: 301836-41-9), and the like. Especially, A83-01 is preferable.

In the present invention, the PKC inhibitor is not particularly limited, and examples thereof include Go6983 (3-[1-[3-(dimethylamino)propyl]-5-methoxy-1H-indole-3-yl]-4-(1H-indole-3-yl)-1H-pyrrole-2,5-dione; CAS registry number: 133053-19-7), GF109203X (3-(1-(3-dimethylamino)propyl)-1H-indole-3-yl)-4-(1H-indole-3-yl)-1H-pyrrole-2,5-dione; CAS registry number: 133052-90-1), and the like. Especially, Go6983 is preferable.

In the present invention, the naïve medium is not particularly limited, and examples thereof include a medium prepared by combining any of additive components such as a non-essential amino acid (NEAA), L-glutamine, 2-mercaptoethanol, antibiotics (for example, streptomycin, penicillin, puromycin, and mitomycin), bovine serum albumin (BSA), and the like, and adding any combination into a basal medium that is preferably a N2B27 medium (a medium obtained by mixing 1:1 of an N2 medium in which N2 supplement has been added to a DMEM/F12 medium and a B27 medium in which B27 supplement has been added to a Neurobasal medium).

In the present invention, the concentration in the medium of various compounds to be added to the naïve medium is not particularly limited. For example, it is preferable that the concentration of LIF is 1 ng/mL to 100 ng/mL; the concentration of an MEK inhibitor is 50 nM to 100 μM; the concentration of a GSK3 inhibitor is 50 nM to 100 μM; the concentration of a cAMP production promoter is 50 nM to 100 μM; the concentration of a TGF-β inhibitor is 10 nM to 100 μM; and the concentration of a PKC inhibitor is 50 nM to 100 μM.

In the present invention, although obvious to a person skilled in the art, it is preferable that culturing is performed in a low-oxygen condition (oxygen concentration: 5%) as the culture conditions for using a naïve medium.

The word "transient" in the step (iii) of the present invention means about five days or more, or about ten days or more, and preferably about 10 to 20 days, and particularly preferably about 10 to 14 days.

In the present invention, the word "allowing expression of the gene introduced in the step (i)" in the step (iii) means, for example, an action of inducing expression of the introduced gene by addition of doxycycline.

In the present invention, examples of the method for determining whether the produced naïve pluripotent stem cells is in a naïve state or not include a method of determining an expression amount of naïve markers of the cells by quantitative PCR, although obvious to a person skilled in the art. Herein, the examples of the naïve marker include DPPA3, ESRRB, TFCP2L1, KLF4, KLF5, and TBX3. Alternatively, the determination can be carried out depending on morphologies, because the primed pluripotent stem cells form mainly a single-layered flat colony, while the naïve pluripotent stem cells form mainly double-layered (dome-shaped) in the colony morphology.

In the present invention, examples the method for determining pluripotency of the produced naïve pluripotent stem cells include a method for determining an expression amount of the pluripotent marker of the cells by quantitative PCR, although obvious to a person skilled in the art. Herein, examples the pluripotent marker include OCT3/4, Nanog, Sox2, SSEA4, and the like. Alternative determination methods include an embryoid body (EB) method, and a teratoma formation method (teratoma).

In the maintaining method of the naïve pluripotent stem cells in the present invention, since induction of expression of an introduced gene is not necessarily needed, it may be or may not be carried out. Preferably, the induction of expression of the introduced gene is not carried out and culturing is performed in a naïve medium in which various compounds are added.

In the present invention, the produced naïve pluripotent stem cells maintain an undifferentiated state, in other words, highly express ESRRB that is one of the naïve markers, and has very high pluripotency. Accordingly, they can be used for (1) induction of differentiation into desired various cells, (2) screening of candidate compounds for pharmaceutical agents using the differentiation-induced cells; (3) generation of tissue for regeneration medicine from the differentiation-induced cells, (4) transplantation of the generated tissue into a patient; (5) an organ regeneration method by transplantation of naïve-state iPS cells into blastocysts, and the like.

In the present invention, cells capable of induction of differentiation of the naïve pluripotent stem cells are not particularly limited, and examples thereof include cardiomyotic cell, a nerve cell, insulin-production cell, glomerulus endothelial cell, mesangium cell, Bowman's epithelial cell, and blood vessel endothelial cell.

In the present invention, a method for differentiation-inducing the naïve pluripotent stem cells is not particularly limited, and examples of a method for differentiation-inducing into the nerve cell include a SDIA (Stromal cell-Derived Inducing Activity) method (Proceedings of the National Academy of Sciences of the United States of America, Vol. 99, No. 3, 1580-1585, 2002).

In the present invention, cells that have been differentiation-induced using naïve pluripotent stem cells can be used for screening drug candidate compounds for various diseases. For example, by adding the drug candidate compounds singly or in combination with other drugs into the differentiation-induced cells, the morphology or functional change of the cells, increase and decrease of various factors, gene expression profiling, and the like, are detected so as to carry out evaluation. Herein, the cells are preferably cells having the same phenotype as that of disease to be treated, and more preferably cells differentiation-induced from the naïve pluripotent stem cells produced from somatic cells derived from a patient having a disease.

In the present invention, tissue can be generated from differentiation-induced cells using naïve pluripotent stem cells, and the generated tissue can be used in the field of the regeneration medicine. For example, damaged nerve tissue can be normalized by replacing the damaged nerve tissue by normal tissue derived from nerve tissue of present invention. This makes it possible to cure diseases derived from damaged nerve cells. Examples of such diseases include Parkinson's disease, Alzheimer's disease, retinal pigmentary degeneration, amyotrophic lateral sclerosis, optic neuromyelitis, optic neuritis, acute disseminated encephalomyelitis, allergic encephalomyelitis, spinal cord damage, transverse myelitis, spinocerebellar degeneration, chronic inflammatory demyelinating encephalopathy (CIDP), Guillain-Barre syndrome, multiple sclerosis, epilepsy, Parkinson's syndrome, Down syndrome, schizophrenic disorder, neurodystonia, Huntington's disease, age-related macular degeneration, and inner ear deafness.

In the present invention, as a transplanting method of the generated tissue into a patient, although obvious to a person skilled in the art, for example, when nerve cells are transplanted, transplantation can be carried out according to the method described in Nature Neuroscience, Vol. 2, No. 12, page 1137-1140, 1999.

EXAMPLES

Hereinafter, the present invention is described in detail with reference to Examples mentioned below, but the present invention is not limited thereto.

Biological Experiment Examples are described below. The advantageous effect of the compound of the present invention was verified based on these experiment methods.

Example 1

Making iPS Cells Naïve
1.1 Culturing of Primed Human iPS Cells

As human iPS cells, WD39 cells (Imaizumi et al. Molecular Brain 2012, 5:35) and 201B7 cells (RIKEN BioResource Center) widely used as a control line were used.

The human iPS cells were cultured using a medium in the primed conditions shown in Table 1 using Mitomycin C-treated or radiation-treated mouse embryonic fibroblast line (STO cells) or mouse embryonic fibroblasts (MEF cells) as feeder cells. Subculturing was performed once every five to seven days. In subculturing, colonies were detached by using a dissociation solution (0.25% Trypsin, 1 mg/ml Collagenase IV, 20% KSR, and 1 mM CaCl2/PBS), finely crushed by pipetting, and then seeded. The iPS cells seeded in a 10-cm dish were subjected to a gene introduction test.
1.2 Generation of Gene-Introduced Cell Line The medium of the iPS cells (10-cm dish) cultured in the conditions of "1.1 Culturing of primed human iPS cells" mentioned above was removed and washed with 7 mL of PBS once, and 1 mL of dissociation solution was then added thereto. After 1 to 2 minutes, the dissociation solution was removed, and 7 mL of PBS was added. The dish was slightly shaken and only the feeder cells were detached, and then PBS was removed. Furthermore, this was washed with PBS once, and 3 mL of the medium of the primed conditions shown in Table 1 was added to the dish, and colonies of the iPS cells were detached using a scraper and then collected into a 15-mL tube. The iPS cells in an amount of 200 g were centrifuged for 5 minutes to remove a supernatant, 1 mL of TrypLE™ Select (Life Technologies) was added and reacted at 37° C. for 5 minutes. To the reacted product, 2 mL of Trypsin Inhibitor (Life Technologies) was added, followed by pipetting 10 to 20 times using P1000 PIPETMAN so as to dissociate single cells. The volume was increased by addition of 7 mL of medium, and the resulting product was allowed to pass through 70-μm Cell Strainer. The iPS cells as single cells were used for gene introduction.

Figure 8:
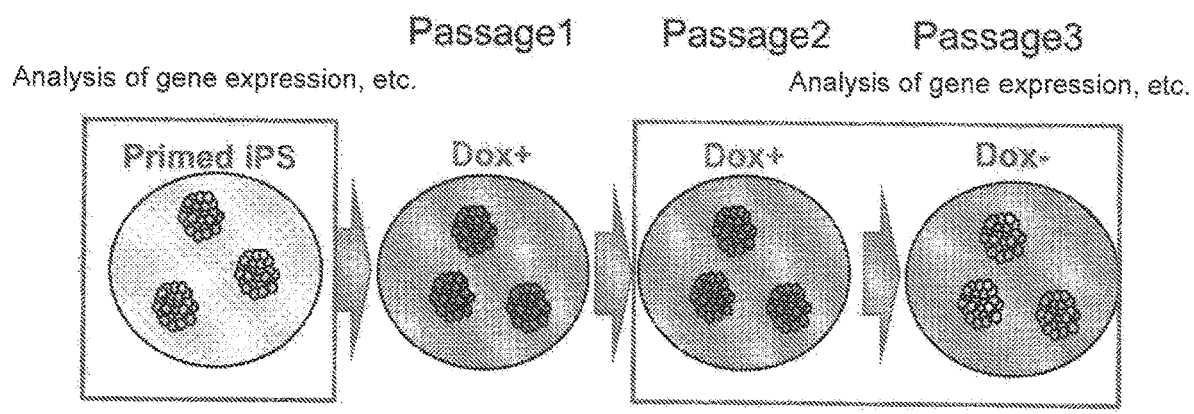
FIG. 8 shows stages of conversion to a naïve state (P1 to P3). P1 represents cells at passage 1, P2 represents cells at passage 2, and P3 represents cells at passage 3.

In the gene introduction, three types of vectors: a reverse tetracycline-controlled transactivator (rtTA) expression vector (rtTA: rtTA-Advanced sequence (Clontech) was used), a PiggyBac Transposase expression vector (see, Proc Natl Acad Sci USA. 2011 Jan. 25; 108(4): 1531-6), a vector which doxycycline-dependently expresses Yamanaka four factors, KLF2 and NANOG, and TOMATO as a fluorescence protein (OKSM, KLF2, NANOG, and TOMATO) were introduced (FIG. 1) using Gene juice (registered trademark) Transfection Reagent (Novagen), and cultured in the same manner as in the above-mentioned "1.1 Culturing of primed human iPS cells." Five to ten days after the gene introduction, doxycycline was added and observed under a fluorescence microscope after 8 to 12 hours had passed. A colony in which fluorescence of TOMATO was observed was determined to be a cell line in which a doxycycline-dependent expression induction system functions, and the colony was picked up and cloned. Later than that, doxycycline was not added, and culturing was performed in the same manner as in the above-mentioned "1.1 Culturing of primed human iPS cells."
1.3 Making iPS Cells Naïve The iPS cells gene-introduced and cloned in "1.2 Generation of gene-introduced cell line" were dissociated into single cells by using a dissociation solution and TrypLE™ Select, and seeded in a 6-well plate at $1 \times 10^5$ cells/well in which MEF cells had been seeded as feeder. At this time, as a medium, 2iLFA+Go6983 medium shown in Table 1 (hereinafter, also abbreviated as "the medium of the present invention") was used, and cultured in low oxygen in a state in which doxycycline (1 μg/mL) was further added so as to induce expression of the introduced gene (Passage 1; P1). Note here that on the first day of the start of making naïve, Y27632 (ROCK inhibitor) was added so as to be 10 μM, resulting in undergoing cell death. On day 5 to 7 after the start of making naïve, subculturing was performed. The medium was removed, and then 350 μL of 0.25% Trypsin-EDTA was added in each well to cause reaction for one minute at 37° C. The reaction was stopped by Trypsin Inhibitor, and then 5 mL of medium was added thereto. Pipetting was carried out several times using PIPETTE AID to detach colonies of iPS cells from a sheet of feeder cells. The colonies were collected in a 15-mL tube. After centrifugation, a supernatant was removed, and 200 µL of medium was added, followed by pipetting using P200 PIPETMAN about 40 times to be dissociated into single cells. All amount of cells were seeded in a new 6-well plate in which MEF cells were cultured as the feeder cells (Passage 2). Also after subculturing, similar to P1, culturing was performed in the condition in which doxycycline was added into the medium of the present invention. Five to seven days after the subculturing, colony morphology of the iPS cells was observed under microscope, and second subculturing was performed. After the second subculturing or later, doxycycline was not added. Five to seven days after the second subculturing, colony morphology of the iPS cells was observed under microscope, and third subculturing was performed. The fourth subculturing or later was performed in the same manner. Note here that at the time of the second and third subculturing, a part of cells at Passage 2 and Passage 3 were collected for qPCR analysis (see FIG. 8).

Example 2

Analysis of Gene Expression Profile by Making Naïve

In this experiment, 201B7 cells were used as the iPS cells.

Cells used for analysis were 201B7 cells cultured in the medium in the primed condition (see "1.1 Culturing of primed human iPS cells"), and 201B7 cells at passage 2 and Passage 3 generated in "1.3 Making iPS cells naïve." RNAs were collected from the respective cells using RNeasy mini kit (QIAGEN), subjected to reverse transcription using ReverTra Ace (registered trademark), and then subjected to qPCR using SYBR (registered trademark) Premix Ex TaqII (clontech). The primer sets are shown in Table 2.

Figure 2:
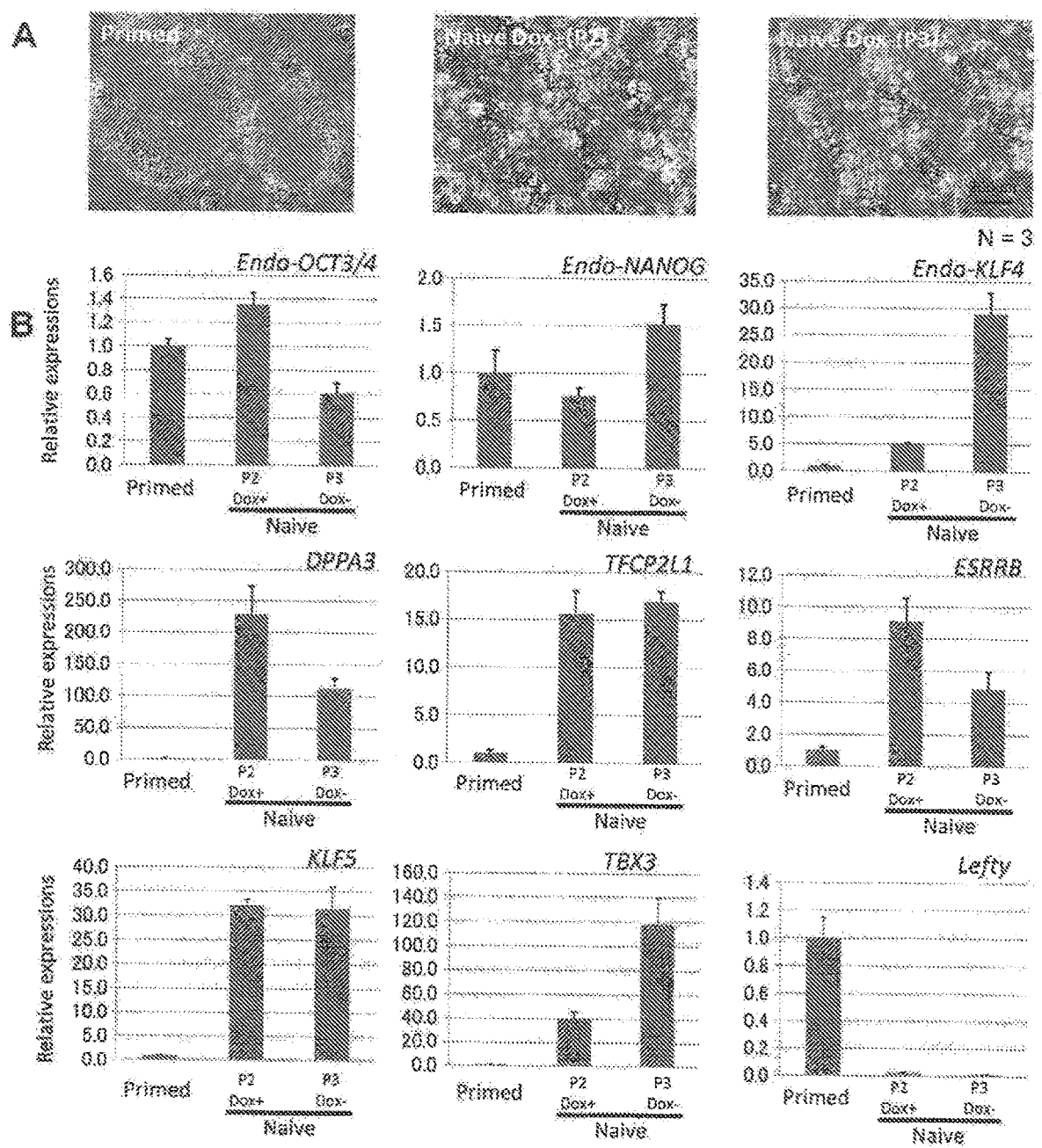
FIG. 2A shows photographs of colonies of cells, respectively.
FIG. 2B shows expression amounts of genes in the cells, respectively. In the drawings, DOX represents doxycycline, P2 represents cells at passage 2, and P3 represents cells at passage 3.

The results are shown in FIG. 2. Expressions of NANOG and OCT3/4 as the pluripotent markers were maintained even a state becomes naïve. Furthermore, in genes such as KLF4, DPPA3, ESRRB, TFCP2L1, KLF5 and TBX3 exhibiting high expression in mouse ES cells as naïve pluripotent stem cells, expression was increased by making naïve. High expression was maintained as compared with in the primed state also after addition of doxycycline was stopped (Passage 3). Furthermore, expression of Lefty as a primed gene marker was reduced by making naïve. From the above-mentioned results, it was found that when the method of the present invention was used, the iPS cells were transitioned to the naïve state at least after passage 2. Furthermore, it was found that after the iPS cells were transitioned to the naïve state, in order to maintain the naïve state, induction of expression of the introduced gene was not needed, and that only the medium of the present invention was sufficient.

Example 3

Effect of Addition Timing of go6983 on Making Naïve

Figure 3:
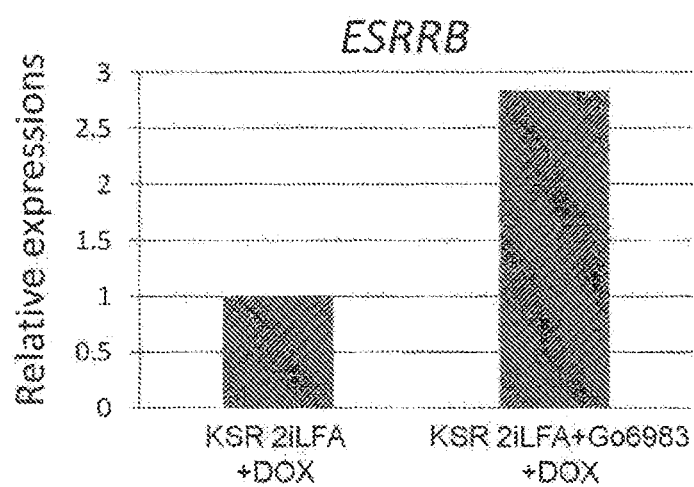
FIG. 3 shows expression amounts of ESRRB genes in 201B7 cells (passage 1) cultured in media, respectively. In the drawing, KSR 2iLFA and KSR 2iLFA+Go6983 represent media shown in Table 1, and DOX represents doxycycline.

In this experiment, an effect of timing of addition of Go6983 on making naïve was considered. A 201B7 cell culture medium at passage 1 in "1.3 Making iPS cells naïve" (a medium of 2iLFA+Go6983 in Table 1) was changed to a medium of KSR 2iLFA of Table 1 or a medium of KSR 2iLFA+Go6983 of Table 1, expression of the introduced gene was induced by addition of doxycycline, followed by culturing in low oxygen. The passage 1 cultured in each condition was collected 5 to 7 days after the subculturing, and subjected to qPCR analysis. Results are shown in FIG. 3. As is apparent from FIG. 3, the iPS cells cultured in a medium into which Go6983 had been added had higher expression of ESRRB. From the results, it was found that the addition of Go6983 at the time of induction of expression of the introduced genes by doxycycline promoted the naïve state of the iPS cells.

Example 4

Effect of Addition of Forskolin and A83-01 on Making Naïve

An ESRRB gene is an important gene that controls self-replication in mouse ES cells (see, Cell Stem Cell, 11,491-504 (2012)). In the present invention, as is apparent from the results of Example 1, regardless of induction of expression of introduced genes, high expression of ESRRB was maintained. On the contrary, in a reset cell described in Non-Patent Literature 3, expression of ESRRB is hardly found (see Non-Patent Literature 3). One of the differences between the condition of the present invention and the condition described in Non-Patent Literature 3 is that in the present invention, Forskolin and A83-01 were added into the medium condition described in Non-Patent Literature 3. Then, the effect of this difference on making naïve (expression of ESRRB and colony morphology) was considered.

In this experiment, a method for making naïve was carried out in the same manner as in the "1.3 Making iPS cells naïve" except that the medium of the present invention (a medium of 2iLFA+Go6983 of Table 1) was used as a medium for considering making naïve, and the medium of 2iL+Go6983 of Table 1 was used as a comparative medium. Evaluation whether or not the cells were made to be a naïve state carried out using ESRRB gene expression and the colony morphology of 201B7 cells at passage 2 and Passage 3 cultured in respective media as indicators.

Figure 4:
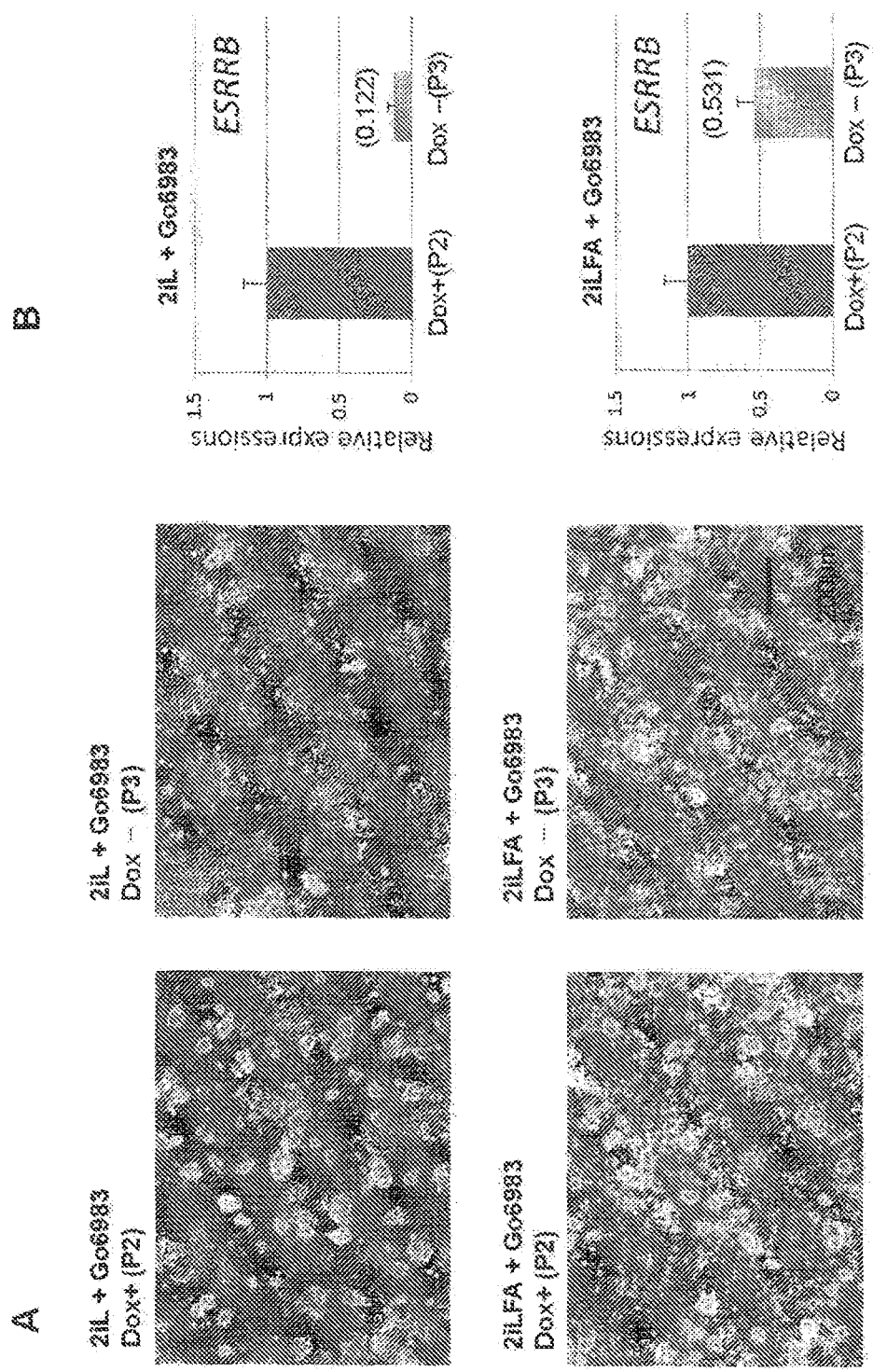
FIG. 4A shows photographs of colonies of 201B7 cells cultured in media (left: passage 2, right: passage 3).
FIG. 4B shows expression amounts of ESRRB genes in the 201B7 cells cultured in media (left: passage 2, right: passage 3). In the drawings, 2iL+Go6983 and 2iLFA+Go6983 represent media represented in Table 1, and DOX represents doxycycline.

Results are shown in FIG. 4. In both media, during addition of doxycycline, the expression of ESRRB was increased, and a colony morphology was dome-shaped similar to the naïve mouse ES cells. However, in the iPS cells cultured in a 2iL+Go6983 medium, when the addition of doxycycline was stopped, the expression of ESRRB was remarkably reduced (about 10% of the expression at the time of addition of doxycycline), and flat colonies, which are characteristics of the primed type, were increased. On the contrary, in the iPS cells cultured in the medium of the present invention (2iLFA+Go6983 medium in Table 1), even after the addition of doxycycline was stopped, the expression of ESRRB was reduced, but the reduction was more slightly as compared with the reduction in 2iL+Go6983 conditions (about 50% of the expression at the time of addition of doxycycline), and the dome-shaped colony morphology was maintained.

From the results, it was found that the addition of Forskolin and A83-01 was needed in order to maintain the naïve state of the iPS cells even after stopping the induction of expression of the introduced gene.

Note here that in the Non-Patent Literature 3, Go6983 was added at the timing when doxycycline was removed. However, since this test was focused on the effect of Forskolin and A83-01, Go6983 was added at the time when doxycycline was added as in the method of the present invention. As is apparent from Example 2, expression of ESRRB was higher when Go6983 was added at the time of doxycycline. Therefore, the expression of ESRRB in the reset cell in Non-Patent Literature 3 was further lower than the results of this experiment, its expression was hardly found as is apparent from Non-Patent Literature 3, transcription factor network in the reset cell was weak (see Non-Patent Literature 3). On the contrary, in the naïve iPS cells produced and maintained by the method of the present invention, expression of the transcription factor that is the same as in the naïve mouse ES cells is found, it is considered that the same transcription factor network as in the naïve mouse ES cells is formed. Therefore, it is shown that the naïve iPS cells produced and maintained by the method of the present invention are in the advanced naïve state as compared with the reset cells described in Non-Patent Literature 3.

Example 5

Comparison of Reprogramming Efficiency by Combination of Reprogramming Factors

One of the differences between the condition of the present invention and the condition described in Non-Patent Literature 3 is that in the present invention, the Yamanaka four factors were added to the reprogramming factors described in Non-Patent Literature 3 (KLF2 and NANOG). Thus, the effect of this difference on making naïve (expression of ESRRB) was considered.

Figure 5:
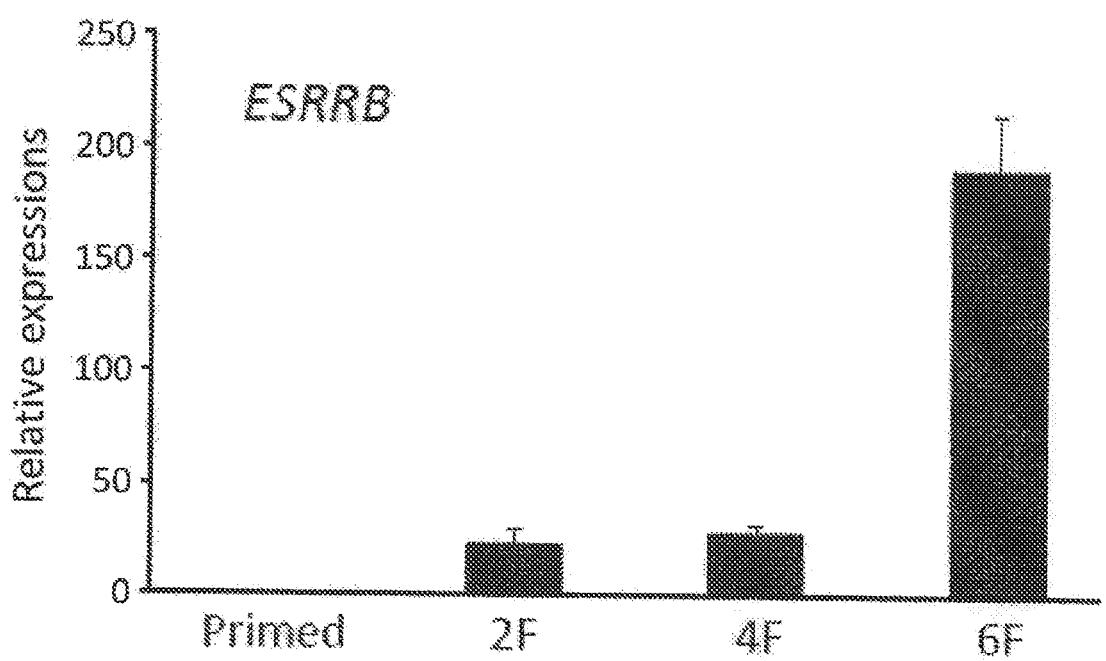
FIG. 5 shows expression amounts of ESRRB genes in combinations of reprogramming factors. In the drawing, 2F represents a combination of a NANOG gene and a KLF2 gene, 4F represents a combination of Yamanaka four factors (an Oct3/4 gene, an Sox2 gene, a Klf4 gene, and a c-Myc gene), 6F represents an NANOG gene, a KLF2 gene and Yamanaka four factors (an Oct3/4 gene, an Sox2 gene, a Klf4 gene, and a c-Myc gene).
Figure 9:
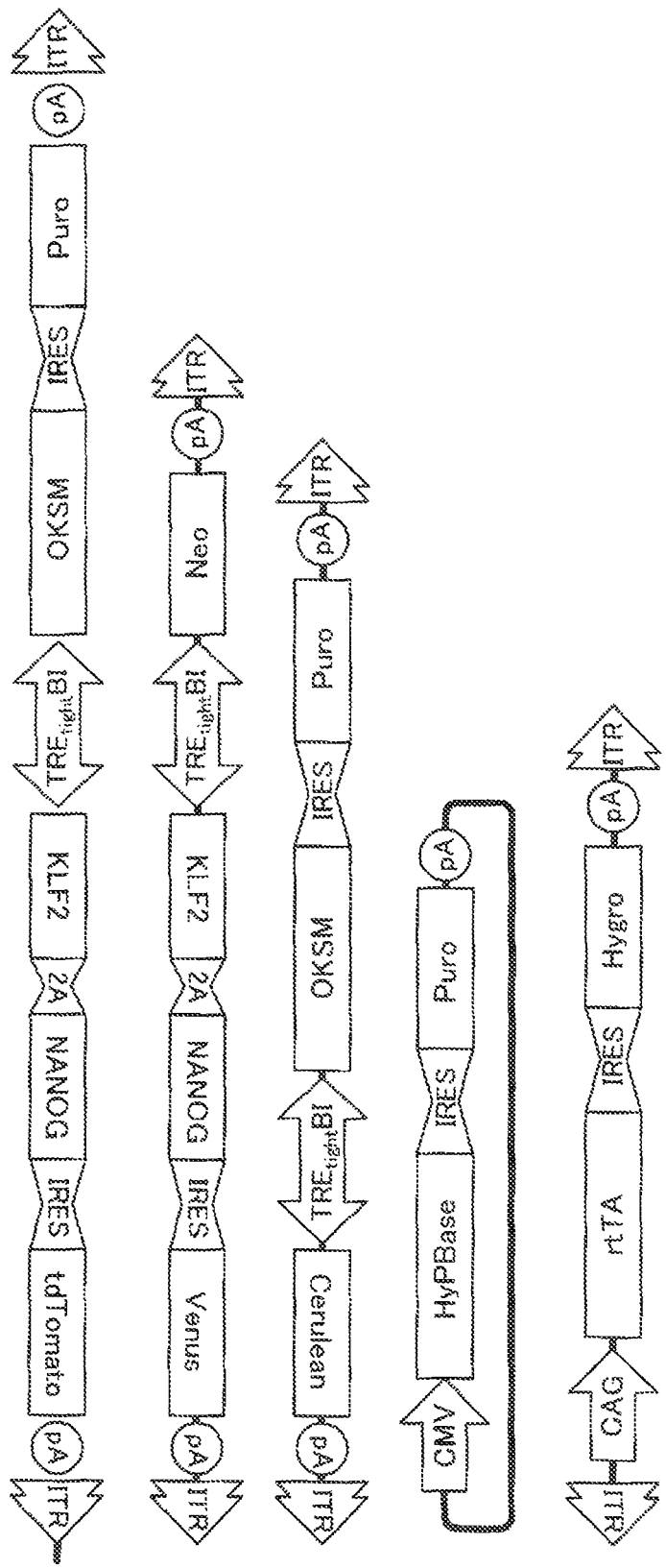
FIG. 9 shows a gene expression vector used for gene introduction in Example 5.

The WD39 cells cultured in the conditions of the above-mentioned "1.1 Culturing of primed human iPS cells" were subjected to gene introduction using a technique similar to that in "1.2 Generation of gene-introduced cell line." In the gene introduction, three types of vectors: a reverse tetracycline-controlled transactivator (rtTA) expression vector (rtTA: rtTA-Advanced sequence (Clontech) was used), a PiggyBac Transposon expression vector (see Proc Natl Acad Sci USA. 2011 Jan. 25; 108(4): 1531-6), and a vector which doxycycline-dependently expresses a reprogramming factor and fluorescence protein were introduced (FIG. 9), and cultured in the same manner as in the above-mentioned "1.1 Culturing of primed human iPS cells." Note here that as the combination of the reprogramming factor and the fluorescence protein, three types: (1) KLF2, NANOG and Venus, (2) Yamanaka four factors and Cerulean, (3) Yamanaka four factors, KLF2, NANOG and TOMATO, were used. The next day to four days after the gene introduction, doxycycline was added. From the next day of the addition of doxycycline, selection by drug was carried out. As the selection, neomycin (100 µg/mL) or puromycin (1 µg/mL) was added depending on the types of doxycycline-dependently expressed resistance genes. Five days after addition of doxycycline, cells were collected and subjected to gene expression analysis by qPCR. As a result, in the cells in which the genes of (3) Yamanaka four factors, KLF2, NANOG and TOMATO had been introduced, expression of ESRRB was synergistically higher than the cells in which (1) KLF2, NANOG and Venus, (2) Yamanaka four factors and Cerulean had been introduced (FIG. 5). Consequently, naïve iPS cells produced by introducing six genes of Yamanaka four factors, KLF2, and NANOG were found to be in a state in which the naïve state was advanced as compared with the reset cells described in Non-Patent Literature 3.

From the above-mentioned results of Examples 3 to 5, the followings were clarified.

(1) Addition of a PKC inhibitor (for example, Go6983) at the time of inducing expression of an introduced gene promotes making naïve.

(2) Introduction of six genes including Yamanaka four factors promotes making naïve as compared with the case of introduction of only two genes of KLF2 and NANOG.

(3) Addition of a cAMP production promoter (for example, Forskolin) and a TGF-β inhibitor (for example, A83-01) allows the naïve state of cells to be maintained.

As mentioned above, naïve pluripotent stem cells (for example, human iPS cells) produced and maintained by the method according to the present invention are in a state in which a naïve state is much further advanced as compared with the reset cells described in Non-Patent Literature 3, and they sufficiently function as the naïve pluripotent stem cells.

Example 6

Neural Differentiation Induction from iPS Cells that were Made Naïve

Figure 6:
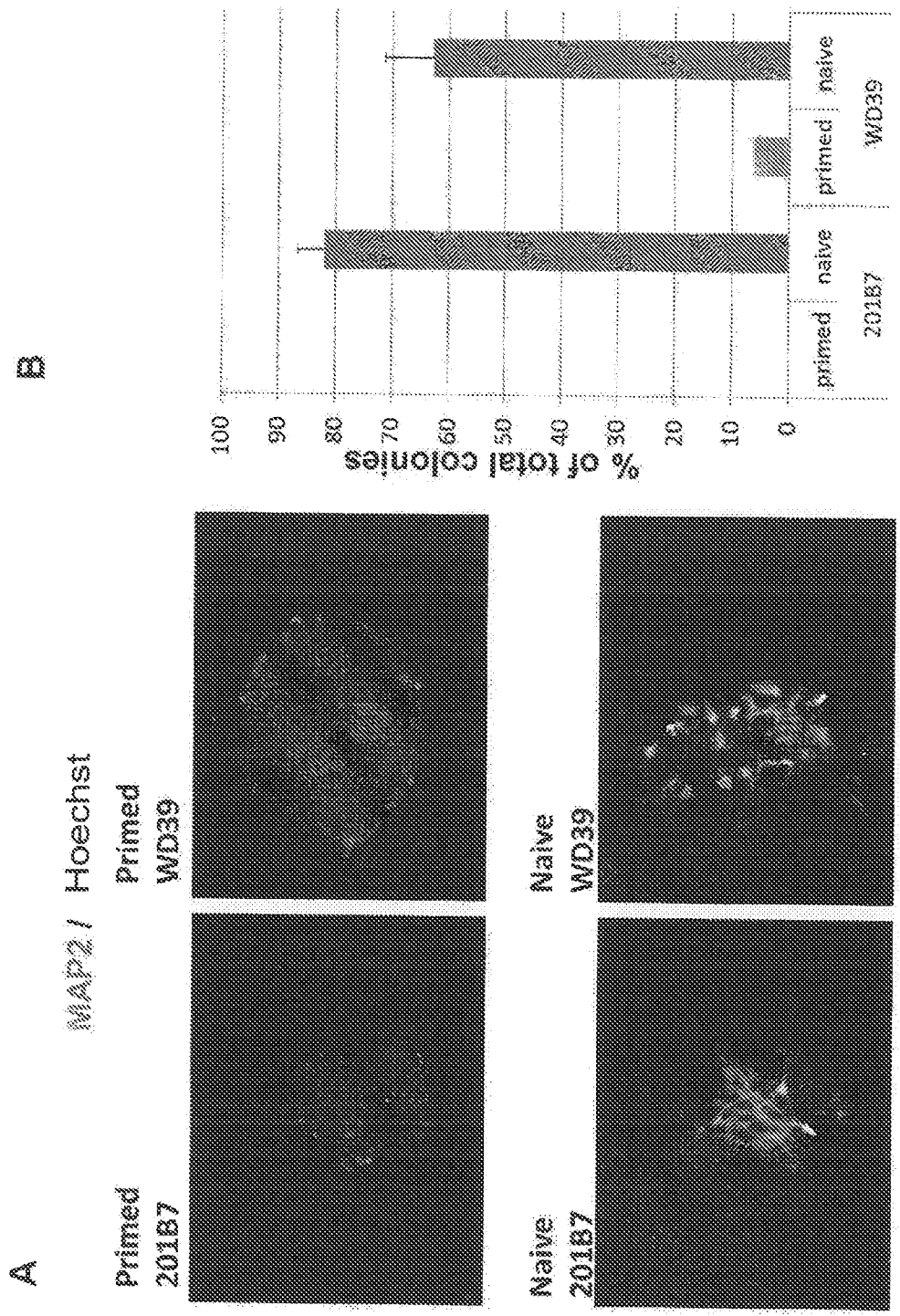
FIG. 6A shows results of cell staining (green: MAP2, blue: nuclear staining by Hoechst) of each iPS cell neural differentiation-induced by the SDIA method for 10 days.
FIG. 6B shows rates of colonies in which MAP2 positive cells are present on day 10 of induction of differentiation of the iPS cells, respectively.

Neural differentiation induction of primed iPS cells and iPS cells that were made naïve were carried out by an SDIA method. The SDIA method is a method for inducing neural differentiation by culturing iPS/ES cells using a mouse stromal cell line (PA6 cells, RIKEN BioResource Center) as feeder cells (see Kawasaki et al. Neuron. 2000 October; 28(1): 31-40). For usual culturing of PA6 cells, αMEM+ 10% FBS was used. When the SDIA method was carried out, the medium was changed to the SDIA medium of Table 1. When the SDIA method was carried out from the primed state, colonies were made into single cells by the same method as in the above-mentioned "1.2 Generation of gene-introduced cell line" but, for the purpose of suppressing the cell death, from one hour before the start of the experiment, Y27632 as a ROCK inhibitor was added so as to be 10 µM. After cells were seeded on the PA6 cells, Y27632 was not added. The cells were seeded to a 12-well plate so that the number of the cells was $2 \times 10^3$ to $2 \times 10^4$ cells/well. When the SDIA method was carried out from the naïve state, cells at passage 3 or Passage 4, which had been generated in the above-mentioned "1.3 Making iPS cells naïve," were made into colonies of single cells by a method using Trypsin-EDTA. Note here that for the purpose of suppressing the cell death, from one hour before the start of experiment, Y27632 as the ROCK inhibitor was added so as to be 10 µM. After the cells were seeded on the PA6 cells, Y27632 was not added. The cells were seeded to a 12-well plate so that the number of the cells was $2 \times 10^3$ to $2 \times 10^4$ cells/well. The cells were fixed by 4% PFA on day 10 of the SDIA method, and MAP2 (antibody M4403, sigma) was subjected to immunohistostaining. Each colony was observed under fluorescence microscope to determine whether or not induction of the MAP2-positive nerve was induced. The results are shown in FIG. 6.

In the iPS cells were made naïve, the rate of colonies in which MAP2-positive cells were present was remarkably higher than that of the primed iPS cells. This result was observed in both 201B7 cells and WD39 cells used. This result showed that the iPS cells that were made naïve by the method of the present invention had excellent differentiation potency.

Example 7

Induction of Differentiation of Astrocyte from iPS Cells that were Made Naïve

Primed iPS cells and iPS cells that were made naïve were substituted to neural differentiation induction by a method via Neurosphere (see Stem Cells. 2008 December; 26(12): 3086-98). When astrocyte differentiation from the primed state was carried out, a colony in a shape of aggregates was detached using a dissociation solution, and floating-culturing was carried out in a medium in which bFGF had been removed from a medium in the primed condition in the Table 1 so as to form an embryoid body. When the astrocyte differentiation was carried out from the naïve state, pipetting was repeated strongly to detach a colony in a shape of aggregates, and culturing was performed in an N2B27 medium (a basal medium of the naïve medium) to form an embryoid body. Note here that the same operation was carried out in the primed iPS cells and iPS cells that were made naïve except for a method of detaching the colony at the time of formation of the embryoid body and a medium. Furthermore, during formation of the embryoid body, in order to promote differentiation into the nervous system, LDN193189 was added so as to be 100 nM. Seven days after the formation of the embryoid body, the embryoid body was collected and 1 mL of TrypLE™ Select was added thereto, and the mixture was reacted at 37° C. for 10 minutes. After 2 mL of Trypsin Inhibitor was added, pipetting was carried out using P1000 PIPETMAN 20 to 30 times so as to be dissociated into single cells. The dissociated cells were adjusted to be $2\times10^5$ cells/ml, and floating-culturing was performed in an MHM medium in which 2% B27 and 20 ng/ml bFGF were added so as to form primary Neurosphere. Seven days after the formation of the primary Neurosphere, Neurosphere was collected, 1 mL of TrypLE™ Select was added thereto, and the mixture was reacted at 37° C. for 10 minutes. After 2 mL of Trypsin Inhibitor was added, pipetting was carried out using P1000 PIPETMAN 20 to 30 times so as to be dissociated into single cells. The dissociated cells were adjusted to be $2\times10^5$ cells/ml, and floating-culturing was performed in an MHM medium in which 2% B27 and 20 ng/ml bFGF were added to form secondary Neurosphere. Seven days after the formation of the secondary Neurosphere, the secondary Neurosphere was seeded onto a cover glass coated with poly-L-ornithine and fibronectin so as to promote differentiation. As a medium for differentiation, an MHM medium containing 2% B27, 2% FBS and 20 ng/ml hLIF was used. Ten days after seeding on the cover glass, the cells were fixed by 4% PFA, immunohistostaining was carried out with respect to βIII-Tubulin as a nerve marker and GFAP as an astrocyte marker (antibody T8660, sigma, and antibody 2.2B10, Thermo Fisher Scientific).

Figure 7:
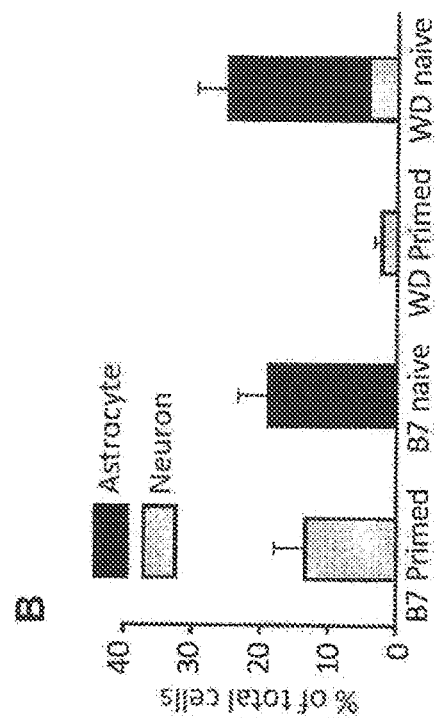
FIG. 7A shows results of cell staining (green: βIII-Tubulin, red: GFAP) of iPS cells, induced neural differentiation by Neurosphere.
FIG. 7B shows rates of differentiation of the iPS cells into astrocyte and nerve cells, respectively.
Figure 7:
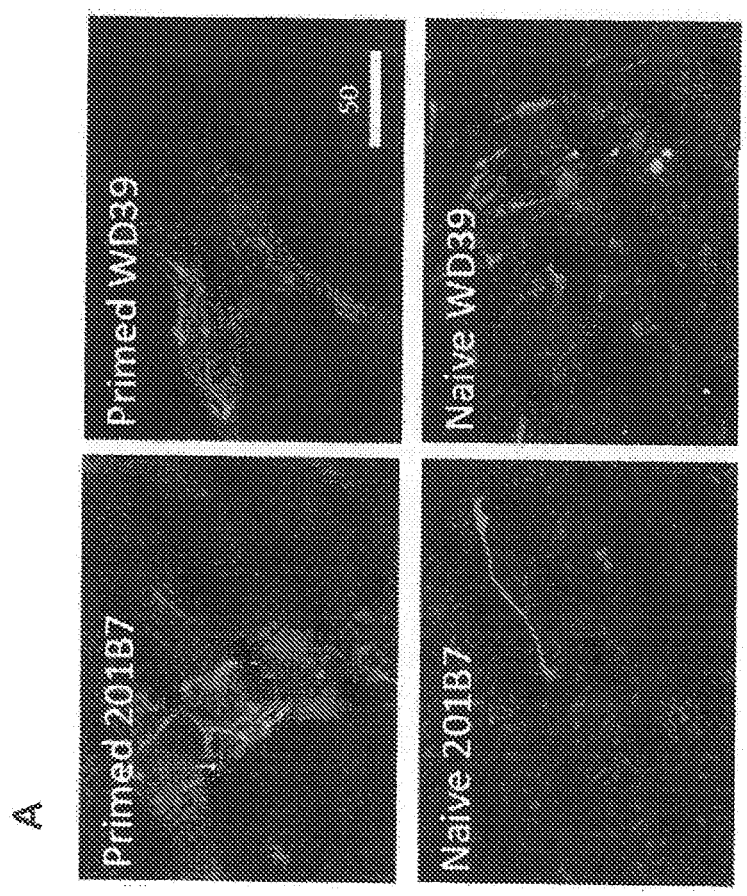

Results are shown in FIG. 7. In the iPS cells that were made naïve, the rate of differentiation into astrocyte was remarkably higher as compared with that of the primed iPS cells. This result was observed in both the 201B7 cells (B7 in the drawing) and WD39 cells (WD in the drawing). The result showed that the iPS cells that were made naïve by the method of the present invention had excellent differentiation potency.

TABLE 1

| Medium Name | Medium | Small molecule, etc. | Culture condition |
| --- | --- | --- | --- |
| Primed condition | DMEM/F12 20% KSR 1% NEAA 1 mM L-glutamine 0.1 mM -2-mercaptoethanol Penicillin/streptomycin | 4 ng/mL bFGF | 37° C. 5% $CO_2$ |
| 2iLFA + Go6983 | DMEM/F12 and Neurobasal (1:1) 1% N2 2% B27 1% NEAA 1 mM L-glutamine 50 μg/mL BSA 0.1 mM 2-mercaptoethanol Penicillin/streptomycin | 10 ng/mL hLIF 1 μM CHIR99021 1 μM PD0325901 5 μM Go6983 10 μM Forskolin 0.5 μM A-83-01 | 37° C. 5% $CO_2$ 5% $O_2$ |
| 2iL + Go6983 | DMEM/F12 and Neurobasal (1:1) 1% N2 2% B27 1% NEAA 1 mM L-glutamine 50 μg/mL BSA 0.1 mM 2-mercaptoethanol Penicillin/streptomycin | 10 ng/mL hLIF 1 μM CHIR99021 1 μM PD0325901 5 μM Go6983 | 37° C. 5% $CO_2$ 5% $O_2$ |
| KSR 2iLFA | KO-D-MEM 20% KSR 1% NEAA 1 mM L-glutamine 0.2 mM 2-mercaptoethanol Penicillin/streptomycin | 10 ng/mL hLIF 3 μM CHIR99021 10 μM Forskolin 1 μM PD0325901 0.5 μM A-83-01 | 37° C. 5% $CO_2$ 5% $O_2$ |
| KSR 2iLFA + Go6983 | KO-D-MEM 20% KSR 1% NEAA 1 mM L-glutamine 0.2 mM 2-mercaptoethanol Penicillin/streptomycin | 10 ng/mL hLIF 3 μM CHIR99021 10 μM Forskolin 1 μM PD0325901 0.5 μM A-83-01 5 μM Go6983 | 37° C. 5% $CO_2$ 5% $O_2$ |
| SDIA medium | G-MEM 10% KSR 1 mM Pyruvate 2 mM L-glutamine 0.1 mM 2-mercaptoethanol | | 37° C. 5% $CO_2$ |

TABLE 2

| Gene | Forward primer | Reverse primer |
| --- | --- | --- |
| Endo-NANOG | gacactggctgaat ccttcctct (SEQ ID No: 1) | accctccatgagat tgactggat (SEQ ID No: 2) |
| Endo-OCT3/4 | agtttgtgccaggg tttttg (SEQ ID No: 3) | acttcaccttccct ccaacc (SEQ ID No: 4) |
| Endo-KLF4 | gccagaaagcacta caatcatgg (SEQ ID No: 5) | ttggcattttgtaa gtccaggaa (SEQ ID No: 6) |
| Lefty | agctgcacaccctg gacctt (SEQ ID No: 7) | gtcattggtgcttc agggtca (SEQ ID No: 8) |
| DPPA3 | Takara perfect real time (HA216940) | |
| ESRRB | Takara perfect real time (HA095808) | |
| TFCP2L1 | Takara perfect real time (HA193431) | |
| KLF5 | Takara perfect real time (HA224420) | |
| TBX3 | Takara perfect real time (HA142445) | |

INDUSTRIAL APPLICABILITY

The present invention makes it possible to stably produce pluripotent stem cells maintaining characteristics of the naïve state and having pluripotency, and therefore, can be practically applied to clinical use and drug evaluation, and the like.

SEQUENCE LISTING FREE TEXT

SEQ ID NO 1: primer
SEQ ID NO 2: primer
SEQ ID NO 3: primer
SEQ ID NO 4: primer
SEQ ID NO 5: primer
SEQ ID NO 6: primer
SEQ ID NO 7: primer
SEQ ID NO 8: primer

The invention claimed is:

1. A method for producing a naïve pluripotent stem cell from a primed pluripotent stem cell, comprising:
   (a) introducing an expression vector containing a polynucleotide encoding Nanog, Klf2, Oct3/4, Klf4, c-Myc, and Sox2, into the primed pluripotent stem cell, and
   (b) culturing the cell obtained in (a) in a medium containing LIF, a MEK inhibitor, a GSK3 inhibitor, a cAMP production promoter, a TGF-β inhibitor, and a PKC inhibitor under conditions for expression of the Nanog, Klf2, Oct3/4, Klf4, c-Myc, and Sox2, to produce naïve pluripotent stem cell,
   wherein the naïve pluripotent stem cell shows (i) an increased expression of ESRRB and one or more of KLF4, DPPA3, TFCP2L1, KLF5, and TBX3 and (ii) a reduced or loss of expression of Lefty gene, compared to the primed pluripotent stem cell.

2. The method for producing a naïve pluripotent stem cell according to claim 1, wherein the primed pluripotent stem cell of (a) is a primed induced pluripotent stem cell or a primed embryonic stem cell.

3. The method for producing a naïve pluripotent stem cell according to claim 1, wherein the primed pluripotent stem cell of (a) is a primed human induced pluripotent stem cell or a primed human embryonic stem cell.

4. The method for producing a naïve pluripotent stem cell according to claim 1, wherein the primed pluripotent stem cell of (a) is a primed human induced pluripotent stem cell.

5. The method for producing a naïve pluripotent stem cell according to claim 1, wherein the MEK inhibitor of (b) is PD0325901, the GSK3 inhibitor is CHIR99021, the cAMP production promoter is Forskolin, the TGF-β inhibitor is A83-01, and the PKC inhibitor is Go6983.

6. The method for producing a naïve pluripotent stem cell according to claim 1, wherein the medium of (b) is an N2B27 medium.

7. A method for producing a naïve pluripotent stem cell from a primed pluripotent stem cell, comprising
   (a) introducing an expression vector containing a polynucleotide encoding Nanog, Klf2, Oct3/4, Klf4, c-Myc, and Sox2 into the primed pluripotent stem cell; and
   (b) culturing the cell obtained in (a) under conditions for expression of the Nanog, Klf2, Oct3/4, Klf4, c-Myc, and Sox2 in the presence of a PKC inhibitor to produce naïve pluripotent stem cell,
   wherein the naïve pluripotent stem cell shows (i) an increased expression of ESRRB and one or more of KLF4, DPPA3, TFCP2L1, KLF5, and TBX3 and (ii) a reduced or loss of expression of Lefty, compared to the starting primed pluripotent stem cell.

8. The method for producing a naïve pluripotent stem cell according to claim 7, wherein the primed pluripotent stem cell of (a) is a primed induced pluripotent stem cell or a primed embryonic stem cell.

9. The method for producing a naïve pluripotent stem cell according to claim 7, wherein the primed pluripotent stem cell of (a) is a primed human induced pluripotent stem cell or a primed human embryonic stem cell.

10. The method for producing a naïve pluripotent stem cell according to claim 7, wherein the primed pluripotent stem cell of (a) is a primed human induced pluripotent stem cell.

* * * * *

```
                              SEQUENCE LISTING

<160> NUMBER OF SEQ ID NOS: 8

<210> SEQ ID NO 1
<211> LENGTH: 23
<212> TYPE: DNA
<213> ORGANISM: Artificial
<220> FEATURE:
<223> OTHER INFORMATION: Forward Primer

<400> SEQUENCE: 1
gacactggct gaatccttcc tct                                             23

<210> SEQ ID NO 2
<211> LENGTH: 23
<212> TYPE: DNA
<213> ORGANISM: Artificial
<220> FEATURE:
<223> OTHER INFORMATION: Reverse Primer

<400> SEQUENCE: 2
accctccatg agattgactg gat                                             23

<210> SEQ ID NO 3
<211> LENGTH: 20
<212> TYPE: DNA
<213> ORGANISM: Artificial
<220> FEATURE:
<223> OTHER INFORMATION: Forward Primer

<400> SEQUENCE: 3
agtttgtgcc agggttttttg                                                20

<210> SEQ ID NO 4
<211> LENGTH: 20
<212> TYPE: DNA
<213> ORGANISM: Artificial
<220> FEATURE:
<223> OTHER INFORMATION: Reverse Primer

<400> SEQUENCE: 4
acttcacctt ccctccaacc                                                 20

<210> SEQ ID NO 5
<211> LENGTH: 23
<212> TYPE: DNA
<213> ORGANISM: Artificial
<220> FEATURE:
<223> OTHER INFORMATION: Forward Primer

<400> SEQUENCE: 5
gccagaaagc actacaatca tgg                                             23

<210> SEQ ID NO 6
<211> LENGTH: 23
<212> TYPE: DNA
<213> ORGANISM: Artificial
<220> FEATURE:
<223> OTHER INFORMATION: Reverse Primer

<400> SEQUENCE: 6
```

-continued

```
ttggcattttt gtaagtccag gaa                                    23

<210> SEQ ID NO 7
<211> LENGTH: 20
<212> TYPE: DNA
<213> ORGANISM: Artificial
<220> FEATURE:
<223> OTHER INFORMATION: Forward Primer

<400> SEQUENCE: 7
agctgcacac cctggacctt                                         20

<210> SEQ ID NO 8
<211> LENGTH: 21
<212> TYPE: DNA
<213> ORGANISM: Artificial
<220> FEATURE:
<223> OTHER INFORMATION: Reverse Primer

<400> SEQUENCE: 8
gtcattggtg cttcagggtc a                                       21
```